United States Patent [19]

Richards et al.

[11] Patent Number: 5,769,879
[45] Date of Patent: Jun. 23, 1998

[54] MICROWAVE APPLICATOR AND METHOD OF OPERATION

[75] Inventors: William F. Richards, Tuscon, Ariz.; Peter LeVay, Santa Barbara, Calif.

[73] Assignee: Medical Contouring Corporation, Henderson, Nev.

[21] Appl. No.: 480,620

[22] Filed: Jun. 7, 1995

[51] Int. Cl.$^6$ .................................................. A61N 5/02
[52] U.S. Cl. ........................ 607/101; 607/154; 607/156
[58] Field of Search .................................. 607/100–102, 607/154–156; 219/746–748

[56] References Cited

U.S. PATENT DOCUMENTS

| | | | |
|---|---|---|---|
| 3,577,981 | 5/1971 | Kuris | 128/2 R |
| 3,589,363 | 6/1971 | Banko et al. | 128/276 |
| 3,958,559 | 5/1976 | Glenn et al. | 128/2 V |
| 4,140,130 | 2/1979 | Storm, III | 607/154 |
| 4,397,313 | 8/1983 | Vaguine | 128/399 |
| 4,527,550 | 7/1985 | Ruggera et al. | 128/1.5 |
| 4,589,422 | 5/1986 | James et al. | 607/155 |
| 4,589,424 | 5/1986 | Vaguine | 607/154 |
| 4,638,410 | 1/1987 | Hance et al. | 318/116 |
| 5,101,836 | 4/1992 | Lee | 607/155 |
| 5,143,063 | 9/1992 | Fellner | 128/399 |
| 5,295,955 | 3/1994 | Rosen et al. | 604/22 |
| 5,503,150 | 4/1996 | Evans | 128/653.1 |
| 5,507,790 | 4/1996 | Weiss | 607/100 |
| 5,540,737 | 7/1996 | Fenn | 607/101 |

FOREIGN PATENT DOCUMENTS

| | | | |
|---|---|---|---|
| 3320990 | 12/1984 | Germany | 607/154 |
| 3431314 | 3/1986 | Germany | 607/154 |

*Primary Examiner*—Lee S. Cohen
*Attorney, Agent, or Firm*—Christie, Parker & Hale, LLP

[57] ABSTRACT

An apparatus and method for non-invasive removal of target tissues is disclosed. The apparatus includes a microwave applicator antenna element array for introducing a plurality of cylindrical, quasi-transverse electromagnetic surface waves adjacent the target tissue. Through successive phase shifts, the electromagnetic surface waves are brought to converge on a focal point within the target tissue, thereby elevating the temperature of the tissue. In one application, the microwave applicator is used for reducing fatty tissue within a subcutaneous fatty layer by taking into account the differing dielectric constants of the adjacent skin and muscle layers. By launching a wave trapped between the skin layer and the muscle layers, a converging cylindrical wave is produced which includes a column of high density along a line extending from the skin-fat interface to the muscle-fat interface. The effect of the column of high density is to raise the temperature of adipose cells to a level at which fat cell necrosis occurs. In operation, a cooling bolus coupled to the applicator actively maintains skin surface temperature below a level at which cell damage or discomfort would occur.

23 Claims, 10 Drawing Sheets

MICROWAVE APPLICATOR AND METHOD OF OPERATION

FIELD OF THE INVENTION

This invention relates to a microwave applicator and the operation of that applicator to achieve hyperthermia and, more particularly, to the employment of a microwave antenna array for use in, for example, thermal adipocytolysis for non-invasive reduction of adipose tissue.

BACKGROUND OF THE INVENTION

Hyperthermia involves the heating of living tissues for therapeutic purposes, such as for increasing blood flow to a particular part of the body. Hyperthermia has been used as a method of treating tumors by means of raising the temperature of the tumor locally, or in the region surrounding the tumor. Hyperthermia can also be effective in reducing adipose tissue through fatty cell necrosis.

Electromedical methods and apparatus for removing target tissue have been disclosed in conjunction with various surgical and therapeutic procedures, some of which are non-invasive. For example, U.S. Pat. No. 4,527,550 to Ruggera et al. discloses a radio-frequency diathermy apparatus, including means for localizing the heat focus for eliminating tumor cells. U.S. Pat. No. 4,397,313 to Vaguine discloses a microwave hyperthermia apparatus, including a means for focusing electromagnetic energy at a particular region of the body. U.S. Pat. No. 3,958,559 to Glenn et al. discloses an ultrasonic transducer for focusing ultrasonic waves for non-invasive treatment of internal structures, for example, tumors, within the body.

Although these systems are useful for non-invasive treatment of target tissues, none are specifically directed to the more general application of removing either tumor cells in deeper tissue layers or fat cells within a largely intact subcutaneous fat layer. In fact, each of these systems recognizes the inherent differences between fatty tissue and tumor tissue and teaches the need for avoiding damage to adipose and other normal tissues adjacent to the tumor. Vaguine and Glenn, for example, point to the differing heat tolerance of tumor cells in the context of preserving fatty and other cells adjacent the target tumor cells, not reducing them. Furthermore, the device disclosed by Vaguine uses an element field polarization more appropriate for treating deep tissues below the fat layer, rather than for treating the fat layer itself.

Accordingly, those skilled in the art would desire a generally applicable non-invasive microwave applicator that could be used to induce hyperthermia in living tissue for therapeutic purposes such as either tumor removal or fatty cell necrosis.

SUMMARY OF THE INVENTION

There is, therefore, provided in practice of the present invention a microwave applicator comprising an antenna element array, an electronic housing for enclosing circuit elements for providing and controlling microwave power, and a cooling bolus for conditioning the microwaves and cooling the skin surface upon application of the microwaves for removal of target tissue. The antenna elements are used for generating a transverse electromagnetic surface wave. For preferentially heating target tissue, the applicator includes a control circuit for adjusting the amplitude and phase of the antenna array elements for converging the transverse electromagnetic waves at the target tissue.

In an exemplary application, the applicator can be used to remove adipose tissue through hyperthermia-induced fatty cell necrosis. The method includes the steps of using the applicator to generate a cylindrical, converging, quasi-transverse electromagnetic surface wave within the fat layer by utilizing the differing dielectric and conductivity characteristics of the skin layer and muscle layers surrounding the fat layer. By launching a wave trapped between these layers from all directions surrounding an intended focus, a converging cylindrical wave is produced which includes a column of high density along a focal line within the fat extending from the skin-fat interface to muscle-fat interface. In operation, the amplitude and phase for the individual antenna elements on the microwave applicator are adjusted to move the focal line within a target fat region to be eliminated within the subject. Simultaneously with application, the cooling bolus actively cools the skin surface to prevent skin burns and acute pain. As a given fat region is treated, the applicator is moved and applied over adjacent regions until the desired fat reduction is achieved.

BRIEF DESCRIPTION OF THE DRAWINGS

These and other features and advantages of the present invention will be better understood from the following detailed description of an illustrative embodiment when read in conjunction with the accompanying drawings, in which:

FIG. 9b is a circuit diagram of an alternate embodiment of the control system of FIG. 9a.

DETAILED DESCRIPTION

Figure 1:
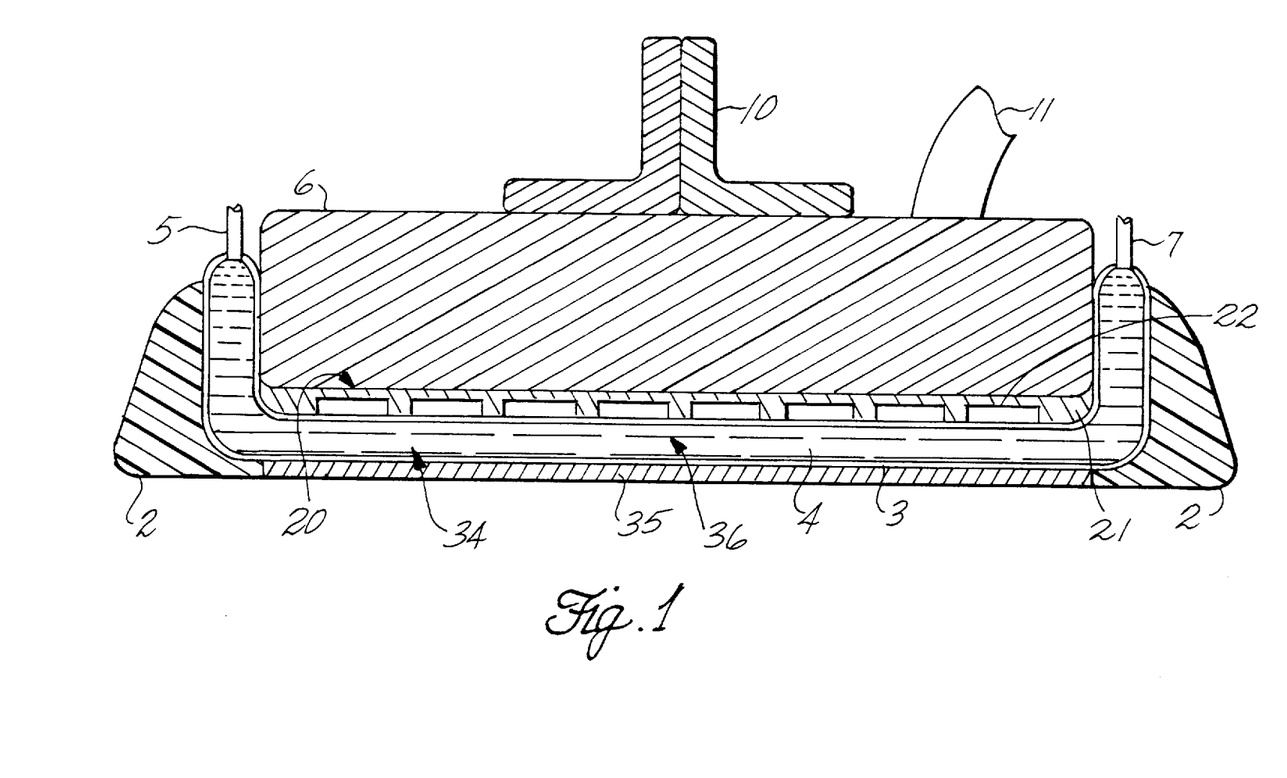
FIG. 1 is a schematic diagram, partly in cross section, of a general purpose therapeutic microwave hyperthermia applicator according to the present invention for non-invasive application of a thermal dose to target tissue.

Referring to FIG. 1, a microwave applicator for inducing hyperthermia in target cells includes an antenna element array 20 having individual antenna elements 22 embedded in a ground plane 21. The array is coupled to an electronic housing, or feed distributional manifold 6, for enclosing electronic components and circuits required for production and control of microwave power. Computer control signals, bias voltages, amplifier power, and possibly microwave power carried through transmission lines are bundled in one or more flexible conduits 11.

For cooling the skin surface during microwave application, the applicator further includes a two-layered bolus 34. In one embodiment (see FIG. 1), a low-impedance layer 35, contacting the skin surface, is formed of a solid high-dielectric material, such as ceramic. The range of dielectric constants suitable for the low impedance is from 40 to 60. A preferred range is from 45 to 55. A high-impedance layer 36 is formed of a thin-walled, low-or-high-dielectric constant vessel 3 through which a cooling fluid 4 is circulated by way of fluid inlet and outlet ports 5, 7. The cooling fluid is chosen to have a dielectric constant much lower than that of the low-impedance layer. The range of dielectric constants suitable for the high-impedance layer is from 4 to 7. A preferred range is from 5 to 6.

The solid portion of the bolus is preferably thin-walled but does not have to be flexible. The liquid portion of the bolus is preferably non-toxic, and should have sufficiently low viscosity so as to allow it to be pumped through the bolus at a rate sufficient for thermal transfer. One suitable liquid includes powdered metals in water, e.g., titanium doped water.

To absorb surface waves incident on the ends of the bolus, part of the high-impedance bolus layer is directed upward along the side of the electronic housing to trap the waves. In addition, the ends of the low-impedance layer are integrally connected to a bounding ring of absorbing terminators 2 made of loss absorbing material for absorbing power in the surface waves incident on the truncation of the applicator. In operation, the bolus acts as a heat exchanger to maintain the temperature of the skin surface below about 140° F. Above this temperature, unwanted damage to cells proximate the skin surface may occur. Preferably, the skin surface temperature is maintained below 120° F. to prevent discomfort. In addition to acting as a heat exchanger, the bolus also conditions the microwaves as they pass from the antenna array through the bolus, and helps to focus the microwaves. For optimal conditioning and focusing, the overall dielectric constant of the bolus is preferably uniform.

Figure 1A:
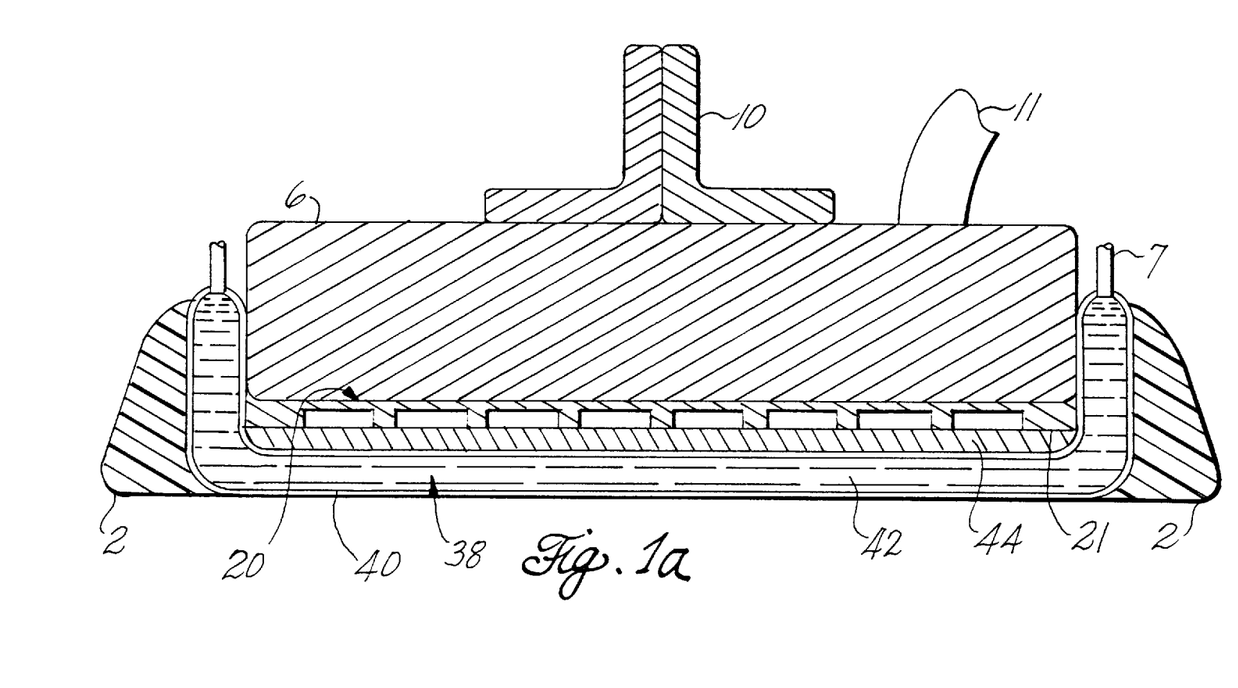
FIG. 1a is a schematic diagram of an alternate embodiment of the microwave applicator of FIG. 1.

Referring to FIG. 1a, in an alternative embodiment of the applicator, the low-impedance layer 38 of the bolus is formed of a high dielectric shell 40 proximate the skin surface through which a high-dielectric cooling fluid 42, such as water, is circulated. The high-impedance layer 44 is formed of a solid lower dielectric material, such as a polytetrafluoroethylene, barium titanate matrix, or by a ferrite material. In the alternate embodiment, the range of dielectric constants suitable for the low-impedance layer and the high-impedance layer are the same as those for the preferred embodiment described above.

The fundamental principle of operation of the microwave applicator is to generate a plurality of cylindrical quasi-transverse electromagnetic surface waves proximate the target tissue. Through successive phase shifts, the waves are brought to convergence, thereby producing a column of high energy density within the target tissue. The effect of the column of high density is to raise the temperature of target tissue to a level at which cell necrosis occurs.

Figure 4:
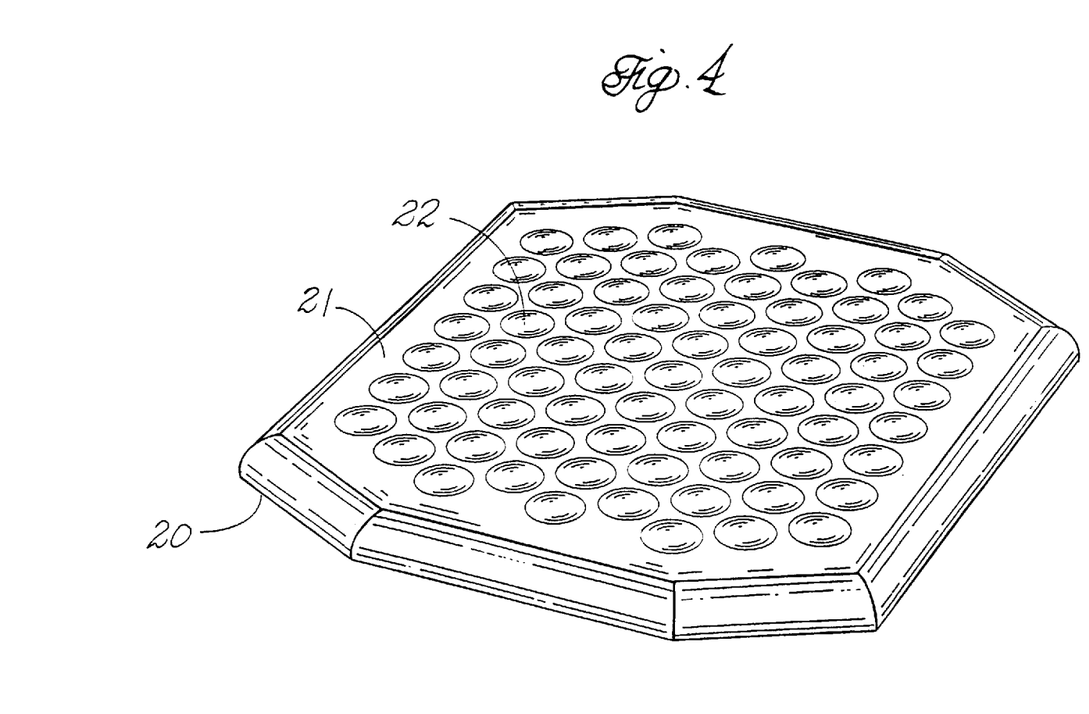
FIG. 4 and 4A are diagrams of a typical arrangement of antenna elements in the microwave applicator of FIG. 1.
Figure 4A:
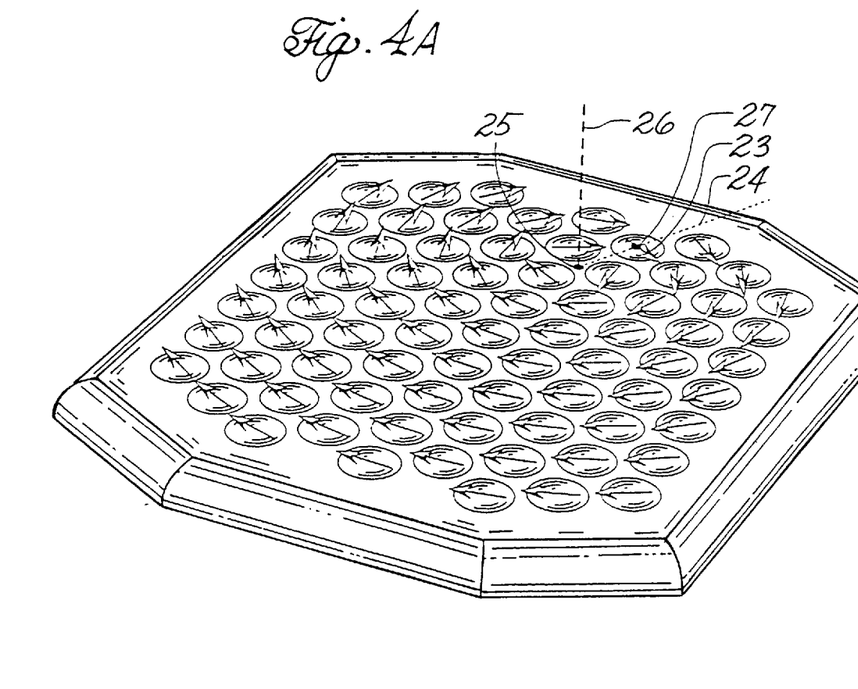

FIGS. 4 and 4A show the underside of the antenna element array 20 that is part of the microwave applicator comprising a ground plane 21 and individual antenna elements 22.

Figure 5:
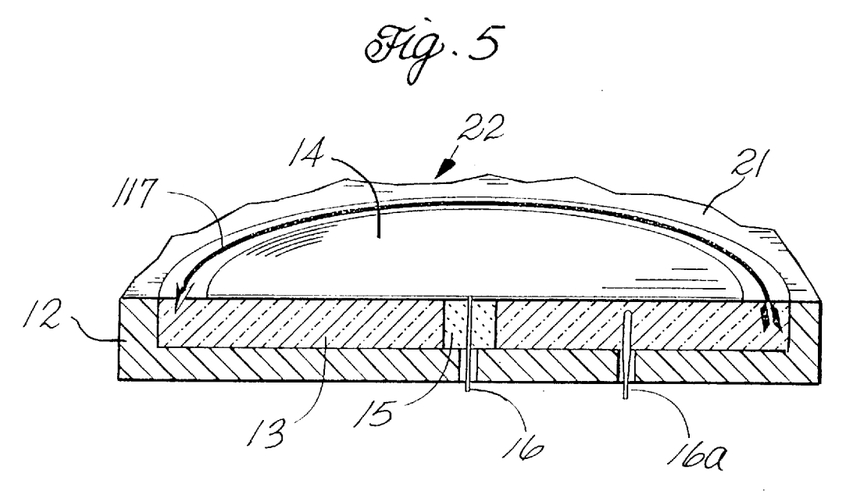
FIG. 5 is a diagram of a typical antenna element used in a preferred embodiment of the present invention.

Referring to FIG. 5, in a preferred embodiment, the individual antenna elements 22 of the array consist of circular microstrip antennas, recessed into the ground plane 21 so that the circular patch 14 is flush with the surface of the ground plane. The elements are fed via a coaxial feed 16 at the geometrical center of the patch through a dielectric or ferrite cylinder 15, whose electrical properties and diameter are chosen along with the electrical properties of the substrate dielectric 13, to cause the element to resonate at the desired operating frequency.

An electric vertical monopole-like mode is produced by the element with an equivalent magnetic current 117 in the gap between the path edge and the ground plane that is uniform in the azimuthal direction. Additional matching of the final amplifier stage is accomplished, if necessary, through an additional conventional matching network to which the coaxial feed 16 is attached. The interior field under the patch, which is proportional to the strength of the equivalent magnetic current 117 (which determines the radiating properties of the element), is sampled via capacitive coupling by the weakly coupled coaxial port 16a. The purpose of the coaxial feed and the feedback loop is to obtain actual data during operation of actual phase and amplitude. The coaxial feed would allow measurement of actual phase and amplitude.

Figure 6:
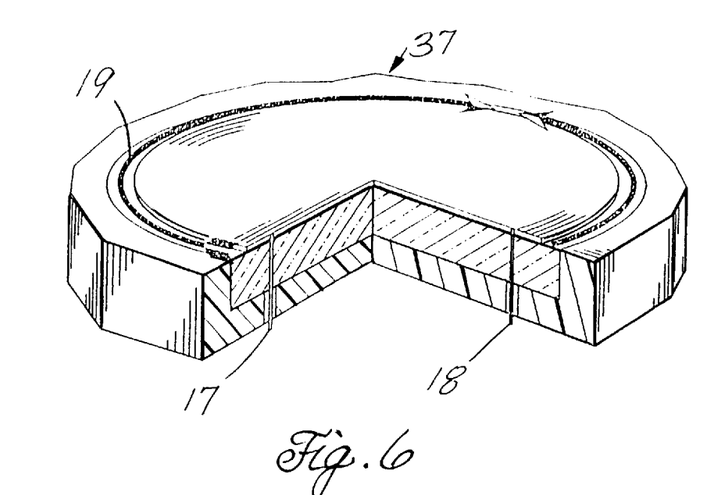
FIG. 6 is a diagram of an alternative embodiment of antenna element.

Referring to FIG. 6, in an alternate preferred embodiment, a dual-feed circular patch antenna 37 is disclosed. The dielectric properties of the substrate material are chosen in this embodiment to resonate the element in a horizontal dipole-like mode. In this mode, the equivalent magnetic current 19, produced when the antenna is fed at coaxial feed port 18, undergoes a change in direction along a nodal plane that bisects the circular patch. A second coaxial feed 17 is placed in this nodal plane. The second feed is capable of independently exciting a similar magnetic current distribution rotated, however, 90° about the center of the patch. This rotated magnetic current produces an electric field in tissue whose transverse component (the component parallel to the plane of the patch) is orthogonal to the corresponding component produced by the other feed. Thus, by simultaneously feeding ports 17 and 18, any state of polarization can be produced.

The first preferred embodiment described above has the advantage of simplicity, requiring half the number of amplifiers, feed ports, and phase shifters as the alternate preferred embodiment. It also has the advantage of producing only transverse magnetic fields. This is an electromagnetic field which lacks a component of magnetic field perpendicular to the plane of the patch. In contrast, the alternate preferred embodiment produces both transverse magnetic and transverse electric field types, the latter of which lacks the desired component of electric field normal to the tissue planes. FIG. 4a illustrates the direction of average magnetic current in each of the elements that would have to be synthesized using appropriate amplitude and phase adjustment of the two ports of the dual-polarized element to launch a converging quasi-TEM cylindrical wave at the focal line 26. The required direction is obtained by constructing a line 24 between the projection 25 of the focal line 26 onto the aperture plane and the center 27 of a given dual-polarized element. The average required direction of magnetic current 23 is then perpendicular to the line 24. Thus, as the scan point varies within the target tissue, the polarization of the dual-polarized elements will have to be readjusted. The alternate preferred embodiment, however, has the advantage of flexibility for use in various target tissue, including tissue in the adipose layer, or other target tissues or tumors in deeper tissue layers.

Figure 7:
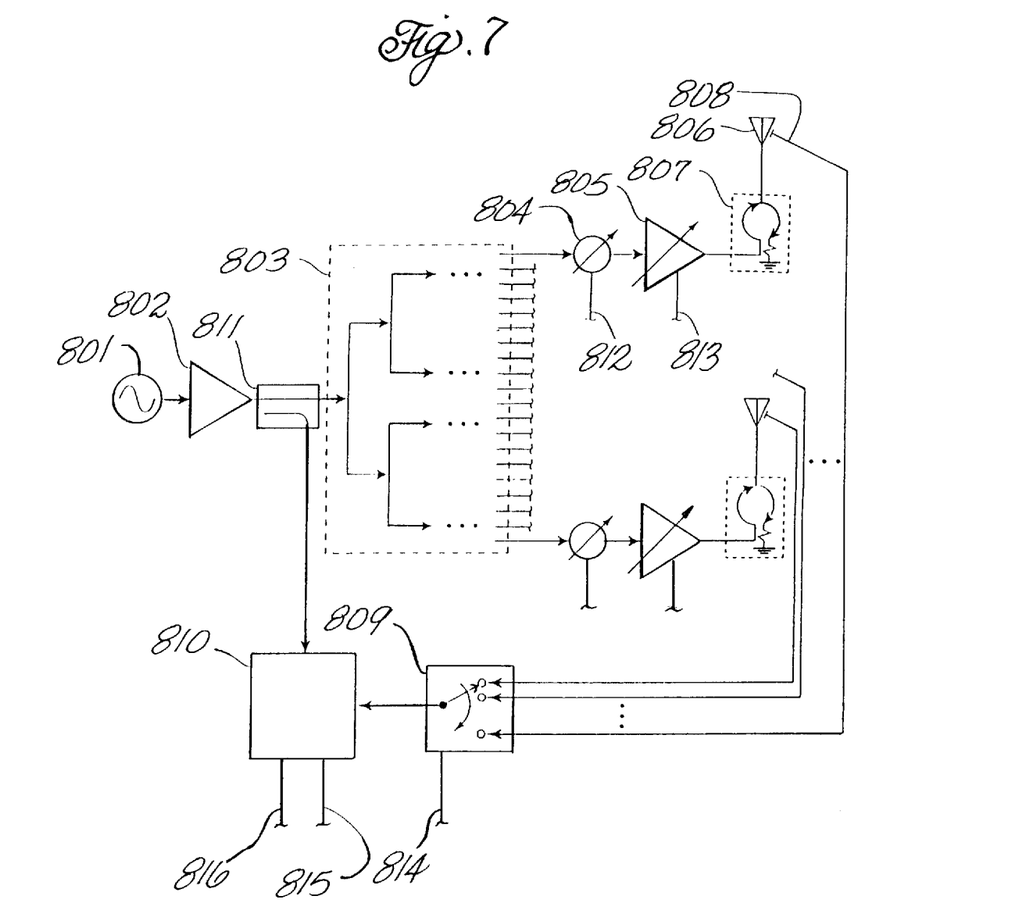
FIG. 7 is a circuit diagram of an exemplary antenna element feed and control system.

The overall system design of the exemplary embodiment using antenna elements 22 as shown in FIG. 5 is illustrated in schematic form in FIG. 7. The output of a common fixed-frequency oscillator 801 is amplified through a fixed gain amplifier 802, whose output is sampled by a directional coupler 811. The output of the main branch of the directional coupler is split by a power-divider 803. This provides a phase-coherent input signal to each of the phase shifters and amplifiers that feed the radiating antenna elements. For example, the output of one branch of the power divider feeds a 0°–360° variable-phase shifter 804 controlled by the dc control voltage in biasing line 812. The output of the phase shifter enters a variable gain amplifier 805, whose gain is controlled by dc control voltage on a biasing line 813.

Depending on the voltage-standing-wave mismatch tolerance of the final output transistor in the variable-gain amplifier 805, an isolator 807 may or may not be included. The output of the amplifier or the isolator, if present, is fed to the input port of an antenna element 806 (element 22 in FIG. 5). The total internal field of the antenna element, which depends both on the actual feed voltage applied to its own input and on the mutual coupling between other antenna elements in the array, is sampled through a weakly coupled sample port 808 (element 16a in FIG. 5). This signal is coupled through a single pole, multithrow microwave switch 809, which is controlled by a control signal on line 814 to a phase-amplitude comparator 810. This comparator sequentially compares the phase and amplitude of each antenna to the phase and amplitude reference provided by the coupled port of the phase shifter 811. The phase and amplitude of each antenna is provided by the coupled port of the phase shifter 811. The phase and amplitude of each antenna is output as dc voltage levels on lines 815 and 816. This information is provided to the controlling computer through analog-to-digital converters. By using an appropriate control algorithm, the bias voltage levels on the phase shifters and the variable-gain amplifiers can be adjusted so that the actual amplitude and phase of the antenna array elements are brought to their desired nominal levels.

Figure 8:
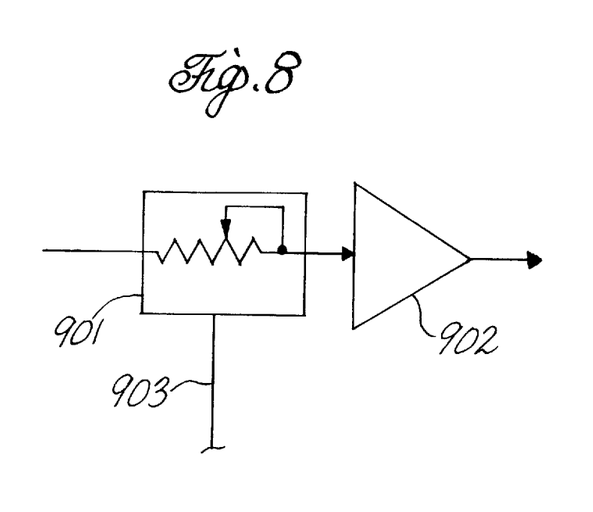
FIG. 8 is a diagram of how to realize the variable gain amplifiers in FIG. 7 using a variable attenuator and a fixed-gain amplifier.

The output power of the variable-gain amplifiers can be controlled by adjusting the bias voltage on one or more amplifier stages through control voltage lines provided in commercially available power modules. Alternatively, the attenuation of a voltage-controlled analog or step attenuator 901, illustrated in FIG. 8, can be controlled by the bias voltage placed on biasing line 903. The output of this attenuator feeds the input of a fixed-gain amplifier 902.

Figure 9A:
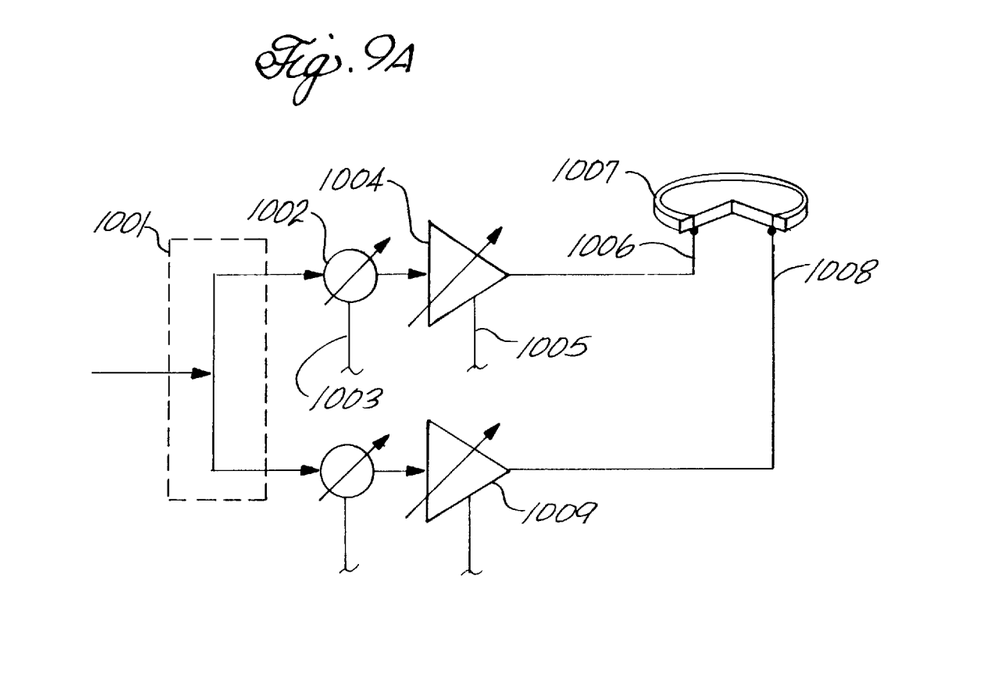
FIG. 9a is a circuit diagram of another exemplary control system for activating particular antenna elements of the type illustrated in FIG. 6.
Figure 9B:
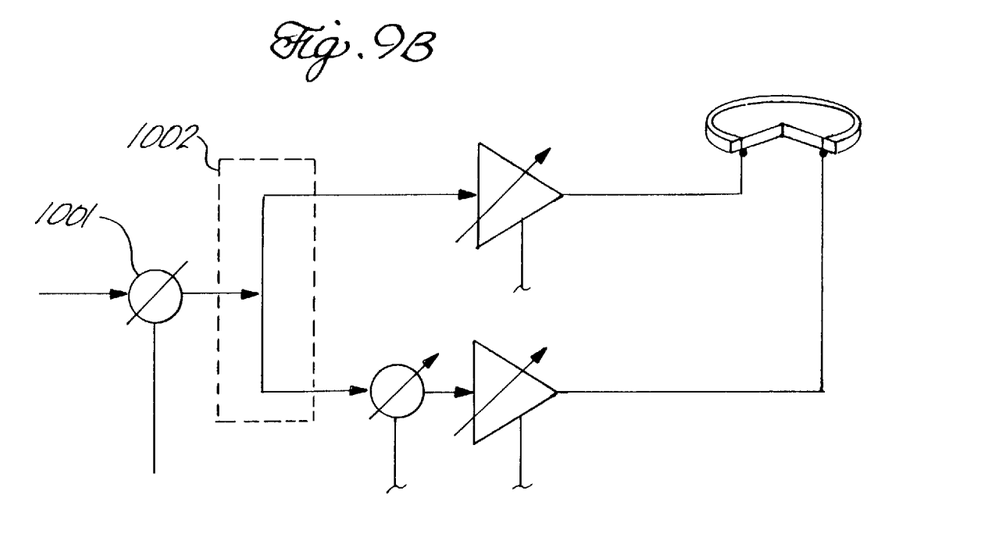

Use of the alternative antenna element 37 illustrated in FIG. 6 requires the feed network illustrated in FIG. 9a. In this case, the output of the main power-divider manifold 803 of FIG. 7 is further divided by a two-way power splitter 1001. The output of each port of the power splitter feeds two identical phase-shifter, amplifier combinations. For example, the output of one port feeds a voltage-controlled variable phase shifter 1002 with bias line 1003. The output of the phase shifter feeds the variable-gain amplifier 1004 with control-voltage line 1005. The output of one amplifier feeds one of the two feed ports 1006 (element 17 in FIG. 6) of a dual-polarized circular microstrip antenna 1007 (element 37 in FIG. 6). The output of the other amplifier 1009 feeds the second orthogonally placed feed port 1008 (18). By adjusting the amplitude and phase of each of the two branches, the net power in each of the two orthogonal polarizations that the antenna element 1007 (37) produces can be independently adjusted, yielding the desired polarization state at the desired amplitude and phase. Alternatively, one of the phase shifters 1001 can be placed between the output of the main power-divider manifold 803 of FIG. 7 and the two-way power divider 1002, as illustrated in FIG. 9b.

As discussed, the microwave applicator according to the present invention is useful for inducing hyperthermia in a variety of applications. The most straightforward application would involve using the microwave applicator to warm a part of a patient's body so as to increase blood flow to the area. Another such application involves the use of the microwave applicator to remove adipose tissue.

Adipose tissue, more commonly known as fat, is formed of cells containing stored lipid. In humans, adipose tissue is widely distributed in subcutaneous tissue located between an outer skin layer and inner muscle layers. Fat cells are relatively large, ranging up to 120 microns in diameter. Adipocytes represent a non-renewing tissue. An increase in adipose mass is mediated by cellular hypertrophy, or enlargement of individual cells, rather than cellular hyperplasia, or increase in numbers of adipocytes.

An excess of adipose tissue, a condition known as obesity, may be undesirable in that it gives rise to various health problems in human beings, both physical and psychological. The former includes an increased risk of heart disease, high blood pressure, osteoarthritis, diabetes, and other unhealthful conditions. The latter can result in a deterioration of an individual's self image and work and social relationships because excess fatty deposits may be perceived by the individual, and those with whom the individual interacts, as having an unsightly appearance. Dieting and behavior modification are helpful for reducing body fat, but it is often difficult to differentially remove fat from selected areas of the body, such as the abdomen or buttocks, while retaining desirable fat in other parts of the body. Moreover, many cannot maintain the regimen of sustained dieting combined with exercise to remove undesired fat from these areas. In such circumstances, spot fat reduction may be needed to eliminate relatively localized fat deposits that may be otherwise difficult to remove by dieting or exercise.

Thus, there exists a need for improved methods of removing adipose tissue, both for treating obesity and for cosmetic purposes. Liposuction has been used primarily for cosmetic fat removal and, occasionally, in an attempt to treat obesity. Liposuction involves purely mechanical means for extracting adipose tissue from the body. This is accomplished by the percutaneous insertion of a tube catheter into the fatty tissue and by application of suction to the proximal end of the tube. Although effective in the cosmetic removal of fat in many cases, the procedure suffers from numerous side effects due to the highly invasive nature of the process. These side effects include serious infection, fat embolism, and complications of anesthesia.

Some non-invasive systems have been disclosed for reducing fatty deposits in humans. These systems, however, suffer from various drawbacks and limitations that make them undesirable or unusable as disclosed for clinical application. For example, U.S. Pat. No. 4,556,442 to Mabuchi et al. describes a massager in which the skin surface is patted repeatedly for eliminating or loosening fat in the subcutaneous layer. The massaging is augmented by feeding warm air into the skin surface being patted. The effectiveness of this device as a means for fat removal is suspect.

U.S. Pat. No. 5,295,955, issued to Rosen et al., discloses a method and apparatus for using microwaves to soften fat cells. Rosen, however, involves using microwaves in conjunction with an invasive liposuction procedure to completely eliminate the cells. More specifically, Rosen discloses a microwave generator for localizing radiation from an antenna into the fatty tissue adjacent the suction portion of the liposuction catheter. The microwaves are used to heat and soften the adipose tissue so less mechanical force is required for its removal. Therefore, although Rosen discloses a method for reducing adipose tissue using microwaves, this method and apparatus still suffers from the disadvantages of invasive procedures involved in liposuction.

U.S. Pat. No. 5,143,063, issued to Fellner, discloses a method for removing adipose tissue from the body by focusing radiant energy, such as RF, microwave, or ultrasound energy, toward fat cells. Fellner recognizes that fatty cell necrosis ("death") can be achieved by causing disruption within the adipose structure, e.g., through hyperthermia. However, Fellner fails to disclose an apparatus for implementing the disclosed method in a clinically operable manner. Instead, regarding the destruction of fat cells, Fellner teaches that " . . . one of the above prior art systems may be employed to supply localized or focused radio-frequency energy, microwave energy, or ultrasound energy to the tissue to be destroyed." In the same disclosure, however, Fellner previously points out that the referenced systems had been employed specifically to avoid normal tissue damage, including damage to the subcutaneous fat layer.

In particular, Fellner fails to disclose how the outer skin surface within the microwave path can be cooled sufficiently to prevent skin burns. There is no disclosure on how the microwave or acoustic energy can be focused on the adipose tissue without unduly heating or damaging surrounding subsurface skin structures and muscle layers, or endangering deep viscera. Nor is there any disclosure of how to prevent treatment-limiting, thermal-induced acute pain or discomfort. Fellner further fails to disclose an apparatus or method for producing the microwaves or for controlling and optimizing the power distribution of the microwaves in the irradiated tissues or for the preferential deposition of energy within the subcutaneous fat layer. Finally, there is minimal disclosure of an effective procedure for limiting and distributing the volume of adipose damage to allow physiological repair mechanisms to remove necrotic cells without inducing potentially disfiguring scarring of subcutaneous tissues.

In the context of fat removal, those skilled in the art would desire a clinically usable apparatus and method for non-invasively reducing or eliminating unhealthful or unsightly adipose tissue without the undesirable side effects of liposuction and without the potential dangers of hyperthermia devices specifically designed to treat tumors.

Figure 2:
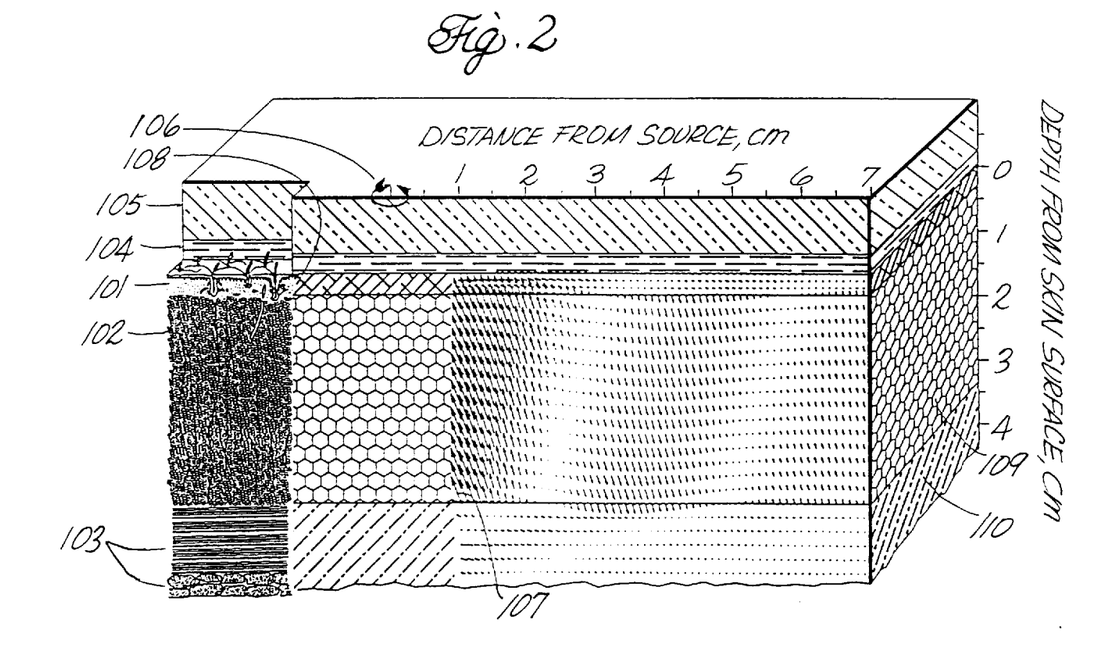
FIG. 2 is a schematic diagram depicting skin with its adnexa, the subcutaneous fat layer, and a portion of the underlying muscle layers.
Figure 3:
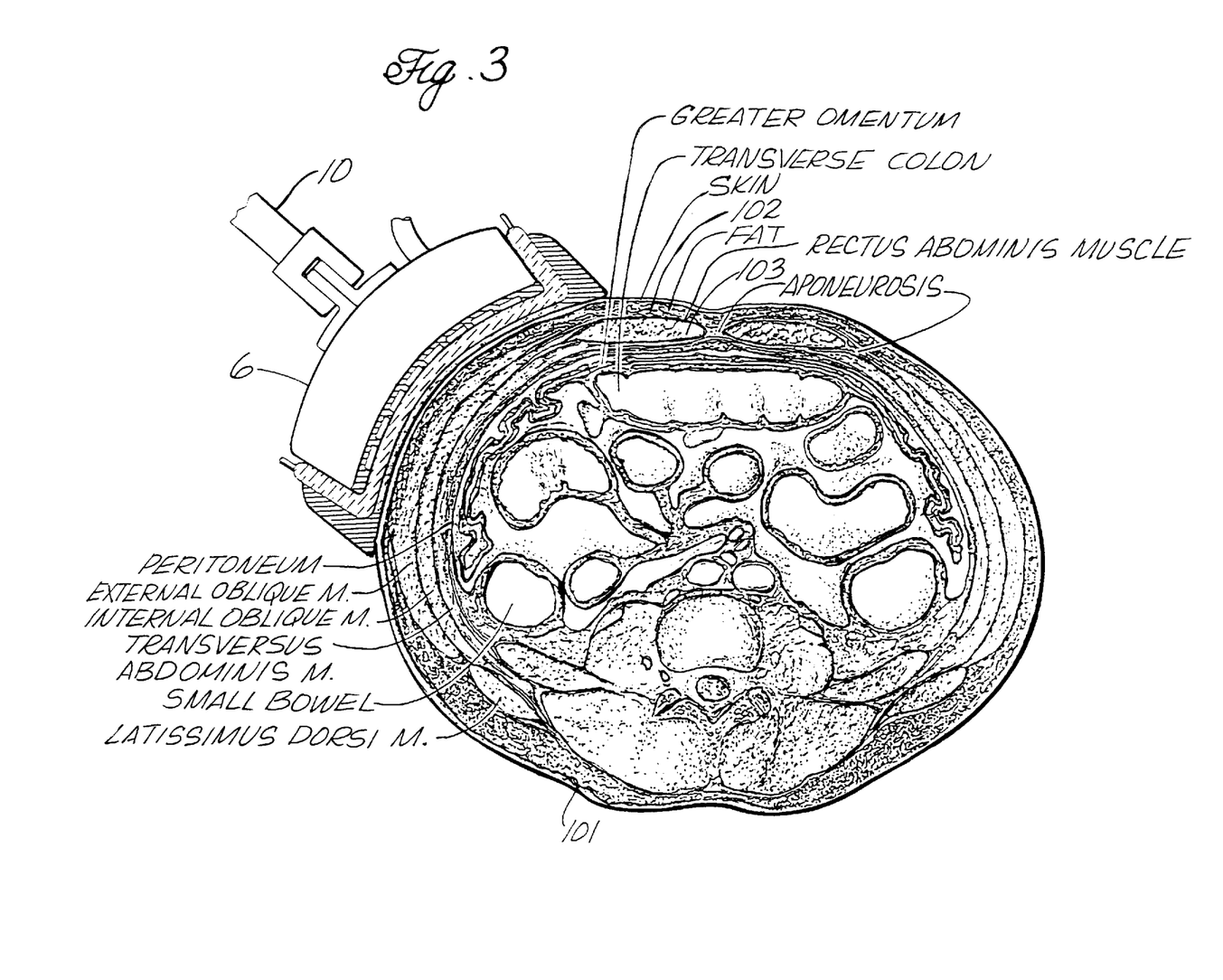
FIG. 3 is a diagram of a microwave applicator according to the present invention and a cross-sectional view of a typical human abdomen showing the skin, subcutaneous fat layer, underlying muscle layers, and viscera in conjunction with a microwave applicator according to the present invention.

The microwave applicator according to the present invention can be used to effectively remove fat cells by inducing hyperthermia in the adipose layer without the use of invasive procedures and without damage to surrounding normal tissue in the adjacent skin and muscle layers. FIGS. 2 and 3 show cross-sections of a typical human body showing the skin layer 101, the muscle layers 103, and the fat layers 102. Also shown are the skin-fat interface 104 and the muscle-fat interface 107. For fat removal, the fundamental principle of operation of the present invention is the generation of a cylindrical converging quasi-transverse electromagnetic surface wave within the fat layer by taking into account the differing dielectric constants and heat capacities of the tissues in the adjacent skin and muscle layers. As shown in FIG. 3, the microwave applicator may be designed with a curved surface to fit against body contours.

The antenna element arrays shown in FIGS. 5 and 6 are both sufficient to induce hyperthermia in the adipose layer. The embodiment of FIG. 5 produces an electric field component that is perpendicular to the plane of the patch, which is most important for the application of preferentially heating the fat layer. The embodiment of FIG. 6 is useful for treating deeper tissues, although it can be used for heating the fat layer by coupling to converging cylindrical waves.

In an exemplary embodiment, assuming a fat layer thickness of 3 cm, the dimensions of the bolus are about 21 cm×21 cm. In a preferred embodiment, optimal excitations for the antenna elements are determined as a function of fat-layer thickness and the dimensions of the bolus. Mathematica software code for identifying the optimal excitations for the adipose tissue reducing application is attached hereto as Exhibit A.

The dimensions of the housing for the exemplary embodiment are about 20 cm×20 cm and the overall dimensions of the antenna array are about 15 cm×15 cm. In the exemplary antenna array, there are 73 individual antenna elements. Each antenna element has a radius of 0.76 cm and is about 1–2 mm thick. Preferably, the overall dimensions of the array should be as small as possible to provide spot fat reduction in hard-to-reach areas while still being effective to launch a converging cylindrical surface wave within the fatty layer. At the present time, the limiting constraint for the dimensions of the bolus is the radius of the antenna element. The thickness of the bolus is chosen to optimally condition the microwaves while effectively cooling skin surface during application.

Those skilled in the art would appreciate that various alternations and modifications to the described invention could be made without departing from the scope of the present invention as set forth in the claims. For example, in operation, it is possible to turn off certain antenna elements to access hard-to-reach areas. Also, although described with respect to fatty cell removal, the microwave applicator according to the present invention may be used for general therapeutic purposes involving hyperthermia.

What is claimed is:

1. A microwave applicator for inducing hyperthermia in target tissue comprising:

a plurality of antenna elements arranged in an array for launching a plurality of electromagnetic waves having a polarization adapted for generating a plurality of electromagnetic surface waves; and a control system including amplitude and phase adjusting elements coupled to the antenna array elements for converging the electromagnetic surface waves at the target tissue, thereby heating the target tissue.

2. The apparatus of claim 1 wherein the antenna element array comprises:

a ground plane; and wherein the antenna elements are attached to the ground plane, each antenna element comprising a circular microstrip antenna.

3. The apparatus of claim 1 further comprising a heat exchanger coupled to the antenna element array for maintaining temperature of skin surface below about 140° F., the heat exchanger comprising:

a low-impedance layer formed of a solid dielectric material; and a high-impedance layer coupled to the low-impedance layer including a vessel through which fluid is circulated.

4. The apparatus of claim 1 further comprising a heat exchanger coupled to the antenna element array for maintaining temperature of skin surface below about 140° F., the heat exchanger comprising:

a low-impedance layer including a shell through which fluid is circulated; and a high-impedance layer formed of solid dielectric material coupled to the low-impedance layer.

5. The apparatus of claim 1 wherein each of the electromagnetic surface waves generated by the antenna element array comprises an electric field component polarized substantially perpendicular to an interface between a skin layer and an adipose layer of a human body.

6. The apparatus of claim 1 wherein the control system and antenna elements are adapted for enabling the antenna element array to generate a plurality of quasi-transverse electromagnetic surface waves.

7. The apparatus of claim 1 wherein the phase adjusting elements comprise a phase shifter for causing successive phase shifts in the antenna elements through which the electromagnetic surface waves are brought to converge on a focal point within the target tissue.

8. The apparatus of claim 1 wherein the control system and antenna elements are adapted for enabling the antenna element array to generate surface waves that become sandwiched in an adipose layer of a human body located substantially between a skin layer and a muscle layer of the human body as a function of dielectric constants of the skin layer, the adipose layer and the muscle layer.

9. The apparatus of claim 1 further comprising a heat exchanger adjacent the array of antenna elements, the heat exchanger including means for conditioning waves produced by the antenna elements.

10. A microwave applicator for inducing hyperthermia in target tissue comprising:
a plurality of antenna elements arranged in an array for generating a plurality of electromagnetic surface waves; and
a control system including amplitude and phase adjusting elements coupled to the antenna array elements for converging the electromagnetic surface waves at the target tissue, thereby heating the target tissue;
wherein each antenna element comprises a dual-feed patch antenna for resonating the antenna element in a substantially horizontal mode.

11. A method for non-invasively removing target tissue disposed at least partially within an adipose layer, the adipose layer located between a skin layer and a muscle layer, the method comprising the steps of:
introducing a plurality of electromagnetic surface waves on a plane dissecting the target tissue, the electromagnetic surface waves comprising an electric field component polarized substantially perpendicular to an interface between the skin layer and the adipose layer; and
converging the electromagnetic surface waves on the target tissue, thereby heating the target tissue.

12. The method of claim 11 wherein the step of introducing the electromagnetic surface waves comprises generating a cylindrical converging quasi-transverse electromagnetic surface wave substantially within the adipose layer.

13. The method of claim 11 wherein the step of introducing the electromagnetic wave comprises generating a wave having selective absorption within an adipose layer.

14. The method of claim 11 wherein the step of converging the surface waves includes converging the surface waves to a focal point within the adipose layer.

15. The method of claim 11 wherein the step of introducing a plurality of electromagnetic surface waves comprises applying a microwave applicator to skin surface, the applicator having an array of antenna elements adapted to introduce surface waves that preferentially generate within the adipose layer as a function of dielectric constants of the skin layer, the adipose layer and the muscle layer.

16. A microwave applicator comprising:
a plurality of antenna elements arranged in an array, each element comprising at least two feeds coupled to a dual polarization antenna, the antenna adapted for supporting at least two linearly independent polarization states; and
a control system including phase and amplitude elements coupled to the feeds for enabling independent adjustment of each of the polarization states.

17. The apparatus of claim 16 wherein the antenna element array comprises:
a ground plane; and
wherein the antenna elements are attached to the ground plane, each element comprising a circular microstrip antenna.

18. The apparatus of claim 16 further comprising a heat exchanger coupled to the antenna elements maintaining temperature of skin surface below about 140° F., the heat exchanger comprising:
a first layer formed of a solid dielectric material; and
a second layer coupled to the first layer including a vessel through which fluid is circulated, wherein the heat exchanger includes means for conditioning waves produced by the antenna elements.

19. The apparatus of claim 16 wherein the control system includes means for controlling the linearly independent polarization states to generate waves adapted for treating a tumor.

20. The apparatus of claim 16 wherein the control system includes means for controlling the linearly independent polarization states to generate surface waves that become sandwiched in an adipose layer of a human body located substantially between a skin layer and a muscle layer of the human body as a function of dielectric constants of the skin layer, the adipose layer and the muscle layer.

21. A microwave applicator for inducing hyperthermia in anatomically normal target tissue comprising:
a plurality of antenna elements arranged in an array for generating a plurality of electromagnetic waves;
a bolus structure adjacent the antenna element array; and
a control system including amplitude and phase adjusting elements for coupling the waves to surface waves which depend upon geometrical and electromagnetic properties of the anatomically normal target tissue and the bolus structure.

22. A microwave applicator for inducing hyperthermia in target tissue comprising:
a plurality of antenna elements arranged in an array for generating a plurality of electromagnetic waves, at least one of the antenna elements comprising a dual-feed patch antenna wherein each feed produces a substantially independent polarization state; and
a control system including amplitude and phase adjusting elements coupled to the antenna array elements for converging the electromagnetic surface waves at the target tissue, thereby heating the target tissue.

23. A method for non-invasively removing target tissue disposed at least partially within an adipose layer, the adipose layer located between a skin layer and a muscle layer, the method comprising the steps of:
generating a cylindrical, converging, quasi-transverse electromagnetic surface wave within the adipose layer as a function of differing dielectric and conductivity characteristics of the skin layer and the muscle layer,
wherein the surface wave is produced by launching a wave trapped between the skin layer and the muscle layer from different directions surrounding an intended focus.

* * * * *

UNITED STATES PATENT AND TRADEMARK OFFICE
CERTIFICATE OF CORRECTION

PATENT NO. : 5,769,879
DATED : June 23, 1998
INVENTOR(S) : William F. Richards; Peter LeVay It is certified that error appears in the above-indentified patent and that said Letters Patent is hereby corrected as shown below:

On the title page,
    Item 56, References Cited, U.S. Patent Documents, change
        "4,638,410 1/1987 Hance et al....318/116" to
        -- 4,368,410 1/1983 Hance et al....318/116 --.
    Column 2, line 43, replace "FIG. 4 and 4A" with -- FIGS. 4 and 4A --.
    Column 8, line 25, replace "alternations" with -- alterations --.
    Column 10, line 51, after "converging" delete "the".

Signed and Sealed this

Second Day of February, 1999

Attest:

Attesting Officer

*Acting Commissioner of Patents and Trademarks*